United States Patent [19]

Newsome et al.

[11] Patent Number: 4,520,014

[45] Date of Patent: * May 28, 1985

[54] TREATMENT OF DIARRHOEA

[75] Inventors: Peter M. Newsome, Worcester Park; Noel A. Mullan, Cranleigh, both of England

[73] Assignee: Beecham Group p.l.c., England

[*] Notice: The portion of the term of this patent subsequent to Mar. 30, 1999 has been disclaimed.

[21] Appl. No.: 350,403

[22] Filed: Feb. 19, 1982

Related U.S. Application Data

[63] Continuation-in-part of Ser. No. 177,365, Aug. 11, 1980, Pat. No. 4,332,814.

[30] Foreign Application Priority Data

Aug. 23, 1979 [GB] United Kingdom ............... 7929434

[51] Int. Cl.³ .................. A61K 33/14; A61K 31/415; A61K 31/165
[52] U.S. Cl. .................................... 424/153; 514/23; 514/401; 514/402; 514/867
[58] Field of Search ............... 424/180, 153, 317, 319, 424/273 R, 324

[56] References Cited

U.S. PATENT DOCUMENTS 4,164,568 8/1979 Bywater .............................. 424/180
4,312,879 1/1982 Lal .
4,332,814 6/1982 Newsome et al. ............. 424/273 R Primary Examiner—Sam Rosen
Attorney, Agent, or Firm—Jacobs & Jacobs

[57] ABSTRACT

Vasoconstrictor α-adrenergic agonists of formula (I)

A-B-C (I)

wherein, A is a 2-imidazoline group or a guanidine group; B is a chemical bond or a linking group one or two atoms in length; and C is a $C_{6-10}$ mono- or bi-cyclic group which is either an aromatic group, a heteroaromatic group containing only one hetero-atom, or a group containing an aromatic moiety; and which group C may be substituted by $C_{1-4}$ alkyl, $C_{1-4}$ alkoxy, halogen or hydroxyl; or salts thereof, are useful in the treatment and prevention of diarrhoea in livestock. Compositions of these compounds are described.

4 Claims, No Drawings

TREATMENT OF DIARRHOEA

This application is a continuation-in-part of our Ser. No. 177,365, filed 8-11-80, now U.S. Pat. No. 4,332,814.

This invention relates to the treatment of diarrhoea in livestock, such as cattle and pigs.

More specifically, this invention relates to the use of a class of α-adrenergic agonists in the treatment of diarrhoea in livestock.

Diarrhoea (also referred to as scours) in livestock can be a severe disease in young animals and can even result in death. The diarrhoea frequently involves colonisation of the small intestine with enteropathogenic strains of E. coli which produce heat stable and/or heat labile enterotoxins. These enterotoxins stimulate fluid secretion in the gut lumen and hence cause diarrhoea. The associated fluid loss may lead to loss of condition, reduced weight gain and often to death. A class of compounds has now been discovered which is effective in the therapy of diarrhoea of this nature.

It should be pointed out that many of the compounds making up this class are known as vasoconstrictors in man, and indeed some of the compounds have been used commercially as nasal decongestants. One of the compounds, Tetrahydrozoline, was disclosed in U.S. Pat. No. 2,842,478 as a potentiator for CNS depressants, as was its use in combination with a CNS depressant for the therapy of animals. However, in this Patent, which was published over twenty years ago, there is no suggestion that Tetrahydrozoline could be used for treating the above described specific type of diarrhoea, and in the Patent it is believed clear that the animals to be treated were pets such as cats and the like, not livestock such as cattle and pigs as in this invention.

It should also perhaps be mentioned that certain compounds of our class were tested primarily for their effects on blood pressure in a paper by Hartmann and Isler, Arch. Exp. Path. Pharmakol, 1939, 192, pages 141-154. In this paper, it is mentioned that some of the compounds have an inhibitory effect on the isolated rabbit intestine. However in the summary of the paper no mention of these results is made, as it is quite clear that the major emphasis of the paper is on blood pressure effects, and of course no suggestion is made that these results might render the compounds of any use in the treatment of diarrhoea, let alone in the treatment of toxin stimulated diarrhoea the therapy of which forms the basis of the present invention. It is believed that the fact that this paper is forty years old, and that to our knowledge no disclosure has since been made to the effect that relevant compounds described in the paper could be used in diarrhoea therapy, clearly demonstrates that the paper provides no teaching for this use of the compounds.

Accordingly, in one aspect, this invention provides a method of treating diarrhoea in livestock, which method comprises administering to the sufferer a compound characterised in being an α-adrenergic agonist having vasoconstrictor activity, and also characterised in having the formula (I):

A—B—C   (I)

wherein:
A is a 2-imidazoline group, or a guanidine group;
B is a direct bond, —CH$_2$—, —CH$_2$O—, —COCH$_2$— or —NH— and
C is a C$_{6-10}$ mono or bi-cyclic group which is either an aromatic group, a heteroaromatic group containing only one heteroatom, or a group containing an aromatic moiety; and which group may be substituted by C$_{1-4}$ alkyl, C$_{1-4}$ alkoxy, halogen or hydroxy; or a salt thereof.

The compound to be administered must meet the three requirements of this invention.

Firstly, the compound must be an α-adrenergic agonist. As is well known, α-adrenergic agonists are compounds which interact with a sub-class of cellular receptors for noradrenaline (α-receptors) and as a result elicit pharmacological actions characteristics of those receptors—see for example R. P. Ahlquist, Am. J. Physiol. 153, 536 (1948).

Secondly, the compound must be a vasoconstrictor. As is well known, vasoconstrictors are compounds which increase peripheral resistance to blood flow by contracting vascular smooth muscle.

Thirdly, of course, the compound must be of the formula (I).

To the skilled man it will be a simple matter to identify compounds meeting these three requirements. Of course many known compounds are also known to have the necessary α-agonist and vasoconstrictor activities, and thus no further work will be needed in identifying such compounds for use in our invention. Whether a given novel compound, or a given known compound of unknown α-agonist and/or vasoconstrictor activity, may be used in our invention is simply determined by routine pharmacological testing.

Examples of suitable known compounds include:

Naphazoline

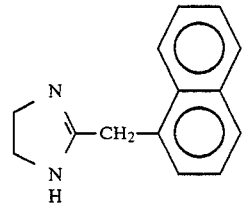

Tymazoline

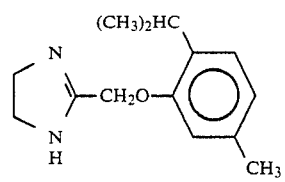

Phedrazine

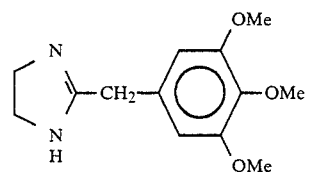

Tetrahydrozoline

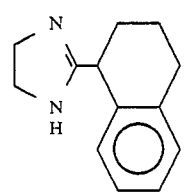

-continued

Xylometazoline 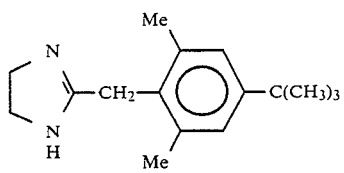

Oxymetazoline 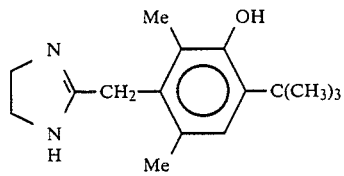

KB 227 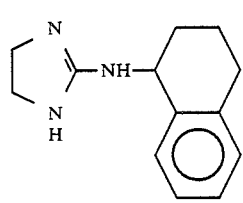

Tenaphtoxaline 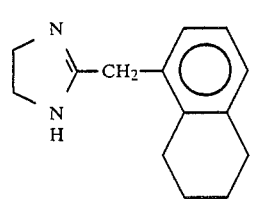

Tramazoline 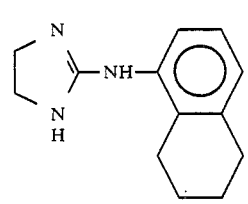

2-methyl Naphazoline 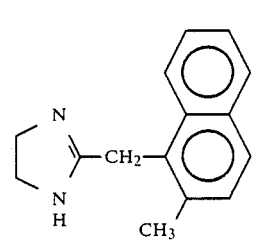

ST91 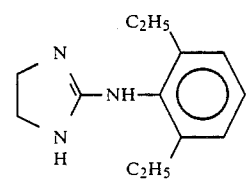

H 1032 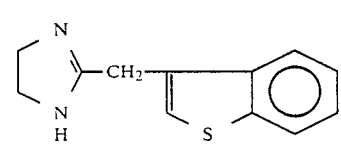

-continued

Clonidine 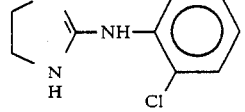

BS100-141 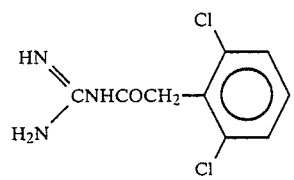

It will be appreciated from the foregoing that suitable examples of the feature B in the α-agonist vasoconstrictors of this invention include —CH₂—, —CO—CH₂—, —CH₂O—, —NH—, and a direct chemical bond. Preferred examples of B include —CH₂—, —NH— and —CO—CH₂—.

Similarly, suitable examples of the $C_{6-10}$ mono- or bi-cyclic group in C in the α-agonist vasoconstrictor of this invention include aromatic groups such as phenyl and naphthyl; partially aromatic groups such as tetrahydronaphthyl; and heteroaromatic groups such as benzothienyl. Preferred examples of this group include phenyl and naphthyl.

Suitable examples of optional substituents for the $C_{6-10}$ mono- or bi-cyclic group in C include methyl, isopropyl, methoxy, hydroxy and chloro. Often, if present, there will be two to four of such substituents in C. When C is substituted phenyl, preferred examples of such groups include those in which one or two of the above named substituents are ortho to the feature B.

In use, the α-agonist vasoconstrictors will be administered in the form of compositions.

Thus one important aspect of this invention provides a veterinary composition for the treatment of diarrhoea in livestock, which composition comprises a compound of the formula (I) as hereinbefore defined and a veterinarily acceptable carrier.

This composition will, of course, be adapted for administration to livestock such as cattle or pigs, preferably to young cattle or pigs.

Thus for example the composition may be a shaped composition, such as a bolus, tablet or capsule. In such cases of course the veterinarily acceptable carrier will be chosen from the usual range of lubricants, dispersants, binders, fillers and the like. As these shaped compositions are for administration to livestock, often they will weight at least 1 g, on occasions at least 2 g.

The composition may also be a dispersion or a solution of the drug in a suitable vehicle for use with an oral doser (this is a well known item of farm equipment, basically comprising a liquid reservoir, a mouthpiece adapted for insertion into animal mouths, and a pump mechanism whereby unit doses can be ejected from the reservoir through the mouthpiece). Conveniently the vehicle will be an oil or water based cream to ensure homogeneity of the unit doses administered.

The invention therefore also provides an oral doser containing a multi-dose of a compound of the formula (I) in a veterinarily acceptable vehicle.

The compounds of the invention may also be added to the animal feed or drinking water. Thus the invention also provides animal feed or animal drinking water containing a compound of the formula (I). It will be convenient to formulate these animal feed and animal drinking water compositions with a multi-dose of the drug so that the animal takes in an appropriate quantity of the drug along with its diet.

With young animals, a particularly useful technique is to blend their milk with the drugs of this invention.

It will also be convenient to present the compositions of the invention as pre-mixes for addition to the feed or driking water.

The compositions of the invention may also be formulated for injection. In such cases the drug chosen is suitably dissolved in water for injection together with agents to adjust tonicity is necessary.

Often it will be appropriate to include in the hereinbefore described compositions a further veterinary medicine such as an anti-bacterial agent, for example amoxycillin.

Also, it is believed that the compounds of this invention can usefully be combined with the oral rehydration composition such as those described in U.S. Pat. No. 4,164,568.

Accordingly the present invention provides, in a particular aspect, a formulation for treating diarrhoea which comprises an effection non-toxic amount of a compound of formula (I) as hereinbefore defined and an oral rehydration composition comprising a pharmacologically acceptable aqueous solution containing at least 0.5% w/v of an actively absorbed monosaccharide, at least 25 mM sodium ions and having an osmolarity less than 500 m Osmolar.

Preferably the compound of formula (I) is selected from the list of compounds given on pages 4 to 7 above.

Preferably the oral rehydration composition further comprises actively-absorbed amino acids and electrolytes.

Active absorption (or active transport) is well known to the skilled man, as are the monosaccharides and amino acids which are actively absorbed. In this regard the reader is referred to standard text books such as 'Medicinal Physiology' by Guyton (published by W. B. Saunders and Company) 4th Edition pages 769 to 771. Of course whether or not a particular monosaccharide or amino acid is actively absorbed may also readily be determined by experiment as for example described in Wilson T. H. 1962 Intestinal Absorption (Saunders, Philadelphia).

To be actively absorbed, monsaccharides must have (a) at least six carbon atoms in their chain (b) a D-pyranose ring structure and (c) an intact hydroxyl group at carbon 2. Thus suitable examples of monosaccharides for use in this invention include the naturally occurring D-pyranoses such as glucose and galactose. Other examples of suitable monosaccharides include naturally occurring D-pyranoses that have been chemically modified whilst retaining the necessary structural features (a), (b) and (c). Examples of such modified monosaccharides include $C_{2-7}$ acylated and $C_{1-4}$ alkylated derivatives, such as acetyl, methyl, ethyl and n- and iso-propyl derivatives. Specific examples include α-methyl glucoside, 3-0-methyl glucose and 6-deoxygalactose.

Preferably the monosaccharide will be glucose or galactose. The monosaccharide of choice for use in this invention is glucose (e.g. dextrose).

Suitably the actively absorbed monosaccharide will account for 40 to 80% of the composition, more suitably 50 to 75% for example 60 to 75% of the composition. Often the monosaccharide will represent at least 65% of the composition.

Suitable examples of actively absorbed naturally occurring amino acids include neutral amino acids such as glycine and alanine and basic amino acids such as arginine. Preferably the amino acid is glycine.

Suitably the amino acid will account for 7.5 to 30% of the composition, preferably 7.5 to 20%, for example 8 to 15% and especially 8 to 12% of the composition.

Suitable electrolytes for such inclusion include salts containing ions such as sodium, potassium, calcium, magnesium, chloride, phosphate, gluconate, sulphate, bicarbonate, carbonate and the like. Other favoured electrolytes for inclusion in the compositions include potassium dihydrogen phosphate, dipotassium hydrogen phosphate, tripotassium phosphate, potassium chloride and the like, with potassium dihydrogen phosphate being particularly suitable.

One particularly preferred electrolyte for inclusion in the composition of the invention is sodium chloride.

Suitably the oral rehydration formulation comprises 10 to 25% electrolytes. Preferably, when sodium chloride is used as electrolyte, it will account for from 7 to 20% of the formulation, for example 10 to 16% of the formulation.

The oral rehydration composition may optionally contain citric acid and/or a salt thereof, representing from 0.5 to 10% of the composition. Suitably 0.5 to 5%, preferably 0.5 to 2%, for example 0.6 to 1.2% of the composition. Often the composition will contain both citric acid and a salt thereof, but the combined amount will not exceed 10% of the composition. Suitable salts of citric acid include sodium and potassium salts such as mono-, di, or tri-sodium or mono-, di- or tri-potassium citrate. Often the composition will include 0.1 to 5% of a salt of citric acid, more suitably 0.1 to 0.5% of such a salt.

The improved oral rehydration formulation may be presented as a dry powder for dissolution in water or a concentrate for dilution in water. Alternatively the formulation may be an orally administrable solution in water, in which case the solution contains at least 0.5% w/v of the monosaccharide and at least 25 mM sodium ions and has an osmolarity of less than 500 m Osmolar. Preferably the formulation also comprises an actively absorbed amino acid and electrolytes.

Most preferably the formulation comprises a compound of formula (I) and an oral rehydration formulation as described in U.K. Pat. No. 1 581 826 and U.K. Patent Application No. 2 012 163 A, U.S. Pat. No. 3,898,328 or Nalin, D. R. & Cash, R. A., *Bull World Health Org*, 43, 361, (1970) and French Pat. No. 2 467 599, which disclosures are incorporated herein by reference.

Advantageously the improved formulation includes a preservative or antioxidant such as ascorbate anions or sodium metabisulphite. When presented in solution the formulation would preferably comprise about 6 mM ascorbate or up to 0.1% w/v sodium metabisulphite.

Advantageously the formulation, when presented as a dry powder, is packaged to exclude air and moisture.

Preferably such compositions contain glucose as the monosaccharide and glycine as the amino acid.

Thus a particularly preferred composition of the invention comprises 60 to 75% glucose, 8 to 15% glycine, 0.5 to 2% citric acid, 0.1 to 0.5% of a salt of citric acid, and 10 to 16% sodium chloride. Such compositions often include 5 to 10% of potassium dihydrogen phosphate.

A second suitable veterinary composition comprises 40 to 80% of an actively absorbed monosaccharide, 7.5 to 13% of an actively absorbed naturally occurring amino acid, and 0.5 to 10% of a citrate salt.

The citrate salt represents 0.5 to 10% of this composition. More suitably the salt will represent 0.5 to 5%, preferably 0.5 to 2%, for example 0.6 to 1.2% of the composition. Suitable examples of citrate salts include sodium or potassium salts such as mono-, di- or tri-sodium, or mono-, di- or tri-potassium citrate.

Thus a particularly preferred composition of the invention comprises 60 to 75% glucose, 8 to 12% glycine, 0.5 to 2% of a salt of citric acid, and 10 to 16% sodium chloride. Such compositions often include 5 to 10% of potassium dihydrogen phosphate.

These compositions suitably contain at least 65% monosaccharide.

If desired the compositions of this invention can contain other substances such as vitamins, minerals, buffers, excipients or the like in conventional manner.

In general the compositions of this invention will be in the form of dry powder for example one which is readily soluble in water. However in an alternative aspect the compositions of this invention will comprise an aqueous solution containing dissolved therein the previously defined solutes in the previously defined relative proportions.

The powders of this invention may be prepared by mixing together the individual components in conventional manner. Once mixed the composition may be put into sachets or other conventional containers.

Optionally the citrate salt or citric acid and the compound of formula I may be presented as a dry powder or solution for inclusion in conventional oral rehydration formulations.

It is frequently advantageous to separate the monosaccharide component from the other components of the composition. This can be effected by using double sachets or other double containers. In such cases components other than the monosaccharide can be mixed and filled into one half of the double sachet and the monosaccharide can be filled into the other half of the double sachet. In such form the compositions of the invention have been found to be particularly stable.

The composition of the invention will normally be administered to the diarrhoeic animal in the form of an aqueous solution, by the oral route. Such solutions may for example contain 20 to 45 g./liter of the composition, suitably 25 to 35 b./liter, for example 30 g./liter. In general calves will be administered from 2 to at least 4 liters per day of such solutions while piglets will normally be administered from a quarter to a one liter per day. The solutions may be administered ad libitum or in two to four or more equal doses per day or by any other similar conventional regime.

It will be realised that in the treatment of severely scouring animals anti-bacterial agents may be administered in conjunction with the compositions of the invention. Examples of suitable anti-bacterial agents for such use include ampicillin, amoxycillin and tetracyclines.

The skilled man will realise that the effective absorption properties found with the liquid compositions of the invention will enable them to be used with advantage whenever liquid absorption by animals is a problem. For example the compositions may be used in treating the general dehydration found in post-operative conditions in animals such as dogs and cats. They may also be administered with advantage to stressed animals, such as recently purchased calves and the like. It is however believed that the compositions of the invention will be of the greatest use in the treatment of diarrhoea in calves.

It will be appreciated that the effective dose of the compounds of the formula (I) will depend in the usual way upon factors such as the severity of the diarrhoea, the weight of the sufferer, the particular compound chosen, and on similar variables. However, as a rough guide we believe that a suitable dose will be within the range 0.05 to 10 mg/kg, which dose may be repeated as and when required.

Clearly the compositions of the invention will contain sufficient compound to enable this effective dose to be administered in convenient manner. Thus by way of example useful dosage units of the composition may contain 0.05 to 500 mg of the compound, more suitably 0.5 to 400 mg. Of course, it will be appreciated that many preferred compositions of the invention are in multi-dose form, as for the therapy of animals it is often most desirable to be able rapidly to treat a number of animals. Such multi-dose compositions will contain by way of example at least 1 g of the compound. Depending on the exact nature of the said multi-dose composition, often it will contain at least 5 g of the compound, and on occasions as much as 20 g.

The following Examples illustrate the anti-diarrhoeal activity of the compounds, and their formulation into veterinary compositions.

Biological Evaluation of the Compounds

The following tests were carried out:

1. Mice

Infant mice are separated from their mothers shortly before use. Animals up to 15 days of age are suitable for use but we normally use animals 7–9 days of age. Groups of animals are dosed with the compound 45 mins prior to oral challenge with 0.05–0.10 ml of culture filtrate prepared from an enteropathogenic strain of *E. coli*. Control animals receive drug vehicle 45 mins prior to challenge with a similar amount of culture filtrate. The compounds are administered orally. Animals are killed two hours later and the entire intestine removed. The ratio of gut weight to remaining bodyweight (GW/BW) is determined from each animal and the increase in this ratio is determined by subtracting 0.06 (GW/BW for untreated mice) from the GW/BW of the animal. Drug treated animals are compared with untreated controls. If the compound has had an effect in inhibiting the fluid secretion caused by the enterotoxin(s) present in the culture filtrate then the gut weight/bodyweight ratio should be reduced in the treated animals. The percentage fluid inhibition is determined from the formula:

$$100 - \left[ \frac{\text{Mean increase in } GW/BW \text{ ratio in treated animals}}{\text{Mean increase in } GW/BW \text{ ratio in control animals}} \right] \times 100$$

2. Rabbits

Infant rabbits 7–10 days old are dosed with the compound under investigation orally 45 min prior to oral challenge with 50 ml/kg bodyweight of material prepared by cell lysis of an enteropathogenic strain of *E. coli*. Control animals receive drug vehicle 45 mins prior to challenge with a similar volume of material. 5-7 Hours after oral administration of the challenge the animals are killed and gut weight/remaining bodyweight ratios calculated and the percentage fluid inhibition determined as above.

3. Piglets 2-4 Day old piglets are dosed with the compound orally 45 min prior to oral challenge with 25 ml of culture filtrate prepared from an enteropathogenic strain of *E. coli*. Control animals receive drug vehicle 45 min prior to challenge with a similar volume of material. Animals are observed for diarrhoea over a 7 hour period and the severity of scour scored on a 0-3 basis for each animal at hourly intervals. The percentage inhibition in treated animals is determined as:

$$100 - \left[ \frac{\text{Mean score of scour in treated animals}}{\text{Mean score of scour in control animals}} \times 100 \right]$$

Results obtained are given in the Table.

| Compound[x] | Structure | Mouse Dose mg/kg | Mouse % Fluid Inhibition | Rabbit Dose mg/kg | Rabbit % Fluid Inhibition | Piglet Dose mg/kg | Piglet % Fluid Inhibition |
|---|---|---|---|---|---|---|---|
| Naphazoline | | 10 | 59 | 10 | 32 | 10 | 88 |
| Oxymetazoline | | 0.1 | 78 | | | | |
| Xylometazoline | | 8.25 | 44 | 20 | 119 | 2 | 44 |
| Tramazoline | | 10 | 44 | | | | |
| Clonidine | | 1 | 42 | 5 | 26 | 0.2 | 64 |
| BS 100-141 | | 1 | 45 | | | 1 | 76 |

| Compound[x] | Structure | Screen | | | | | |
|---|---|---|---|---|---|---|---|
| | | Mouse | | Rabbit | | Piglet | |
| | | Dose mg/kg | % Fluid Inhibition | Dose mg/kg | % Fluid Inhibition | Dose mg/kg | % Fluid Inhibition |
| Lidamidine | HN=C(NHCH₃)−NH−CO−NH−(2,6-dimethylphenyl) | 50 | 33 | 50 | −7 | | |
| 2-Methyl Naphazoline | (imidazoline)−CH₂−(2-methylnaphthyl) | 20 | 82 | | | | |
| ST91 | (imidazoline)−NH−(2,6-diethylphenyl) | 5 | 56 | | | | |
| | | 1 | 22 | | | | |

[x]All compounds tested as hydrochloride salts

These results clearly demonstrate the high level of activity of the Compounds in the reduction of fluid secretion caused by challenge with an enterotoxin from an enteropathogenic strain of *E. coli*.

The activity of the Compounds is highlighted by comparison with Lidamidine, which as can be seen from the Table, is at least five times less active than the Compounds in the mouse test and inactive in the rabbit test.

Lidamidine is a known anti-diarrhoeal, for example as reported in G. N. Mir et. al., Arzneim-Forsch/Drug Res 28 (II), Heft 8a (1978), page 1448, wherein it was alleged inter alia that Lidamidine inhibited intestinal secretion induced by cholera toxin.

A number of compounds allegedly structurally related to Lidamidine, as well as Lidamidine itself, were examined for various pharmacological activities in G. H. Douglas et. al., Arzneim-Forsch/Drug Res. 28 (II), Heft 8a (1978), page 1435. These activities included an anti-diarrhoeal test, but no evidence was presented in this paper in relation to diarrhoea caused by toxin induced intestinal secretion.

4. Anti-diarrhoeal Effect in *E. coli* Infected Piglets

Colostrum deprived piglets were infected on the first day of life with *E. coli* P155 by oral administration of approximately $3 \times 10^9$ organisms. When scour was observed the animals were paired by weight and severity of scour and one animal from each pair was treated with amoxycillin 40 mg p.o. whilst the other animal was treated with 40 mg p.o. +2 mg/Kg p.o. naphazoline hydrochloride in water. The water and naphazoline hydrochloride solutions were coded and dosing and scoring of the severity of diarrhoea were carried out "Blind" as described in the experiments with enterotoxin induced diarrhoea (above).

The following result was obtained:

| | Mean scour score ± S.E.M. (during 6 hrs after treatment) |
|---|---|
| Amoxycillin + water | 2.0 ± 0.2 (n = 14) |
| Amoxycillin + naphazoline HCL | 0.8 ± 0.1 (n = 14) |

The result was statistically significant $P<0.001$ (t test)

5. Calf Thirty-Vella Intestinal Loop Model

In vivo tests were conducted using male castrate calves, each with two surgically prepared Thirty-Vella intestinal loops prepared as described by R. J. Bywater, J. Comp. Path., 80, 565, (1970).

The loops are washed with saline and then a saline bolus is left in the loops for 30 minutes to establish a basal absorptive rate. After 30 minutes the fluid in the loops is removed and measured. Heat stable *E. coli* enterotoxin from *E. coli* strain p16 is added to the loop infusate which is then returned to the loops.

After a further 30 minutes the content of the loops is measured once more and at this time the drug is added to the test loop perfusate.

Toxicity

The compounds have been found to have a satisfactory therapeutic ratio.

| Time (Min. after toxin administration) | Control | Naphazoline 2 mg/Kg | Control | Clonidine 10 μg/Kg | Clonidine 0.8 μg/Kg | Control | BS100-141 1 μg/Kg |
|---|---|---|---|---|---|---|---|
| −30-0 | −9 | −7 | −4 | −5 | −2 | −4 | −4 |
| 0-30 | 24 | 25 | 22 | 20 | 21 | 34 | 36 |
| 30-60 | 24 | 1* | 16 | 2* | 5* | 25 | 13* |
| 60-90 | 20 | 3* | 11 | −1* | 3* | 17 | 10* |
| 90-120 |  |  | 8 | −3* | 1* | 15 | 8* |
| 120-150 |  |  | 8 | −3* | 2* | 13 | 8 |

Inhibition of Toxin Induced Intestinal Secretion in Calf Thiry-Vella Loops

*indicates statistical significance at least at the 5% level (paired t test.)

Formulation of the Compounds for Veterinary Administration

EXAMPLE 1

Naphazoline bolus 10 mg

Boluses of the following composition were prepared:
Naphazoline hydrochloride: 10 mg
Microcrystalline cellulose: 500 mg
Corn starch: 250 mg
Magnesium stearate: 25 mg
Lactose, anhydrous: to 2500 mg The ingredients were passed through a 30 mesh stainless steel screen and blended in a suitable blender. The resultant compression mix was compressed directly on a tabletting machine to give tablets each containing 10 mg naphazoline hydrochloride.

EXAMPLE 2

Xylometazoline Oral Doser 1 mg/g

1 Kg of the following composition was prepared:

| | % by wt. |
|---|---|
| Xylometazoline hydrochloride | 0.1 |
| Aluminium stearate | 6.0 |
| Sunflower oil | to 100 |

The aluminium stearate was dispersed with stirring in a portion of the sunflower oil heated to 115° C. The dispersion was added to the rest of the sunflower oil heated to 140° C. The gel was stirred at 130° C. for 15 minutes and then allowed to cool without stirring to room temperature. The milled xylometazoline hydrochloride was dispersed in the cooled gel base and then passed through a colloid mill to produce a fine, homogenous dispersion. The dispersion was filled into plastic bottles fitted with a dosing pump.

EXAMPLE 3

Clonidine Injection 0.5 mg/ml

1 Liter of the following composition was prepared:

| | % w/v |
|---|---|
| Clonidine hydrochloride | 0.05 |
| Sodium chloride | 0.5 |
| Water for injections | to 100 |

The clonidine hydrochloride and sodium chloride were dissolved in the water for injections and the solution was filtered and filled into glass ampoules. The ampoules were sterilised by autoclaving.

EXAMPLE 4

BS 100-141 Premix

A premix of the following composition was prepared:

| | % by wt. |
|---|---|
| BS 100-141 (2,6-dichlorophenylacetylguanidine hydrochloride) | 1.0 |
| Limestone flour | to 100 |

The ingredients were mixed together in a ribbon blender to give a homogeneous mixture. The premix was mixed into animal feed at the rate of 1 kg per metric ton to provide a concentration of 10 g of BS 100-141 per metric ton.

EXAMPLE 5

Naphazoline Soluble Powder

1 Kg of the following composition was prepared:

| | % by wt |
|---|---|
| Naphazoline hydrochloride | 13.6 |
| Lactose | to 100 |

The naphazoline hydrochloride and lactose were sieved and mixed together in a suitable blender to give a homogeneous powder. The powder was filled into jars. The powder was used at the rate 0.5 g per gallon of drinking water to medicate pigs.

EXAMPLE 6

15 g of the following composition may be prepared by mixing together the ingredients in dry powder form:
Guanfacine: 0.5% by weight
Dextrose (anhydrous): 71.5% by weight
Glycine: 12% by weight
Sodium Chloride: 7% by weight
Potassium Dihydrogen Phosphate: 7% by weight
Citric Acid: 2% by weight The resultant unit-dose composition is dissolved in 500 ml of water.

EXAMPLE 7

80 g of the following composition may be prepared by mixing together the ingredients in dry powder form:
Guanfacine: 0.006% by weight
Dextrose (anhydrous): 66.9% by weight
Glycine: 10.3% by weight
Sodium Chloride: 14.3% by weight
Potassium dihydrogen phosphate: 6.8% by weight
Citric Acid: 0.8% by weight Tripotassium citrate: 0.2% by weight The resultant unit-dose composition is then dissolved in 2500 ml of water.

EXAMPLE 8

The procedures of Examples 6 and 7 may be repeated, but prior to dissolution in water the ingredients are filled into a twin sachet with the dextrose in one part of the sachet and all the other ingredients in the other part of the sachet.

EXAMPLE 9

Each of Examples 6 to 8 may be repeated with otherwise identical compositions containing an orange flavour.

EXAMPLE 10

Each of Examples 6 to 8 may be repeated with otherwise identical compositions containing a lemon flavour.

EXAMPLE 11

Twin sachets may be filled with the following ingredients:

| Ingredient | % | Particle Size μ |
|---|---|---|
| Sachet A (Net weight 19.4 g) | | |
| Glycine U.S.P. | 31.8 | 500 |
| Citric acid (anhydrous) Ph. Eur. | 2.5 | 370 |
| Potassium dihydrogen phosphate N.F. | 21.0 | 350 |
| Potassium citrate Ph. Eur. | 0.6 | milled to <50 |
| Sodium chloride Ph. Eur. | 44.1 | 365 |
| Guanfacine | 0.025 | |
| Sachet B (Net weight 44.6 g) | | |
| Dextrose monohydrate B.P. | 99.85 | |
| Aerosil 200 (Colloidal Silicon Dioxide N.F.) | 0.15 | |
| | 5.8962 g | |

The twin sachets thus formed are then opened and their contents dissolved in B 2 liters of warm water and used to treat a scouring calf.

EXAMPLE 12

1 kg of the following composition may be prepared by mixing together the ingredients in dry powder form:
Guanfacine: 0.006%
Glycine: 10.3
Dextrose (anhydrous): 67.5
Sodium Chloride: 14.3
Potassium Dihydrogen Phosphate: 6.8
Citric Acid: 0.8
Tri-potassium Citrate: 0.2
60 g of the composition is then dissolved in 2 liters of water.

EXAMPLE 13

The following composition may be prepared by a method analogous to that of Example 12:
Glycine: 10%
Guanfacine: 0.007
Dextrose (anhydrous): 71.9
Sodium Chloride: 10
Citric Acid: 5
Tri-potassium Citrate: 3
60 g. of the composition is then dissolved in 2 liters of water.

EXAMPLE 14

For storage, the composition according to Example 12 is prepared in the same manner, but the dextrose (676 g.) was filled into one container and the remaining ingredients (324 g.) were filled into a second container.

EXAMPLE 15

The following formulation may be prepared by a method analogous to that of Example 12.

| | w/w % |
|---|---|
| Sodium Chloride | 11.6 |
| Calcium Gluconate | 2.2 |
| Magnesium Sulfate | 0.6 |
| Monopotassium Phosphate | 8.7 |
| Glycine | 21.2 |
| Guanfacine | 0.006 |
| Dextrose, anhydrous | 55.6 |

EXAMPLE 16

1 k.g. of the following composition may be prepared by mixing together the ingredients in dry powder form:
Guanfacine: 0.006%
Glycine: 10.3%
Dextrose (anhydrous): 67.5
Sodium Chloride: 14.3
Potassium Dihydrogen Phosphate: 6.8
Tri-potassium Citrate: 1.0
60 g. of the composition is then dissolved in 2 liters of water.

EXAMPLE 17

The following composition may be prepared by a method analogous to that of Example 16.
Guanfacine: 0.008%
Glycine: 10
Dextrose (anhydrous): 71.9
Sodium Chloride: 10
Tri-potassium Citrate: 8
60 g. of this composition is then dissolved in 2 liters of water.

EXAMPLE 18

For storage, the composition according to Example 16 is prepared in the same manner, but the dextrose (676 g.) is filled into one container and the remaining ingredients (324 g.) are filled into a second container.

EXAMPLE 19

To 60 g. of a composition prepared according to Example 12 is added 400 mg. of amoxycillin.

EXAMPLE 20

1 k.g. of each of the following compositions may be prepared by mixing together the ingredients in dry powder form:

| | 51 % | 52 % | 53 % |
|---|---|---|---|
| Guanfacine | 0.005 | 0.006 | 0.008 |
| NaCl | 31.33 | 14.8 | 15 |
| Glucose | 50.4 | 66.77 | 60.9 |
| Glycine | 10.11 | 9.39 | 12 |
| Citric acid | 3.00 | 1.33 | 3 |
| $K_3$ citrate | 5.06 | 1.23 | 3 |

-continued

| | 51 % | 52 % | 53 % |
|---|---|---|---|
| KH$_2$PO$_4$ | — | 6.38 | 6 |

EXAMPLE 21

Compositions according to each of Examples 6 to 20 may be produced having, instead of Guanfacine, a compound selected from the following list:

| | | |
|---|---|---|
| Naphazoline | Oxymetazoline | H 1032 |
| Tymazoline | KB 227 | Clonidine |
| Phedrazine | Tenaphtoxaline | |
| Tetrahydrozoline | Tramazoline | |
| Xylometazoline | 2-methyl Naphazoline | |
| | ST 91 | |

We claim:

1. A composition adapted to be administered to livestock for the treatment or prevention of diarrhoea which composition comprises an oral rehydration formulation and an amount effective to treat diarrhoea of a compound which is an α-adrenergic agonist and which has vasoconstrictor activity and is selected from formula (I).

$$A—B—C \qquad (I)$$

wherein: A is an optionally substituted 2-imidazoline group or an optionally substituted guanidine group, said substituents, when present, being C$_{1-4}$ alkyl, C$_{1-4}$ alkoxy, halogen or hydroxy; B is a direct bond or —CH$_2$—, —CH$_2$O—, —COCH$_2$— or —NH—; and C is a C$_{6-10}$ mono- or bi-cyclic group which is either an aromatic group, benzothienyl, or a group containing an aromatic moiety; and which group C may be substituted by C$_{1-4}$ alkyl, C$_{1-4}$ alkoxy, halogen or hydroxyl; or a salt thereof.

2. A composition according to claim 1 wherein said oral rehydration formulation comprises a pharmacologically acceptable aqueous solution containing at least 0.5% w/v of an actively absorbed monosaccharide, at least 25 mM sodium ions and having an osmolarity less than 500 m Osmolar.

3. A composition comprising a dry powder suitable for dissolution in water and amounts of a compound of formula (I), an actively absorbed monosaccharide and sodium ions such that, on dissolution, said dry powder provides a formulation according to claim 1.

4. A composition according to claim 1, wherein said compound of formula (I) is selected from the group consisting of

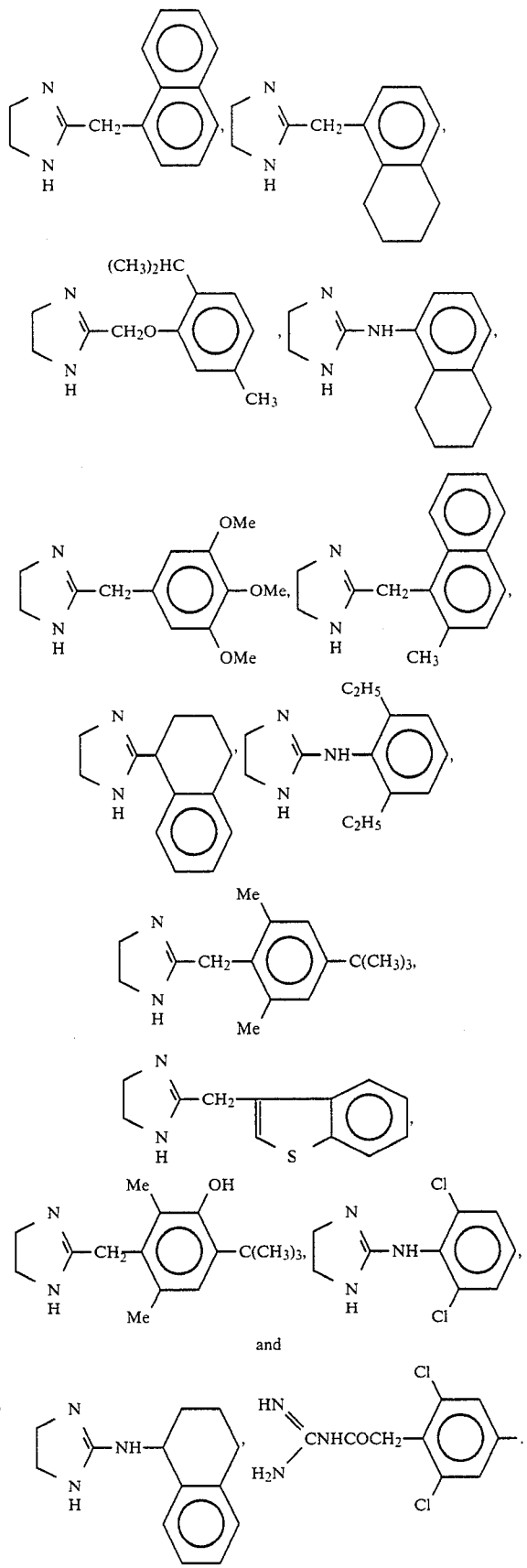

* * * * *

UNITED STATES PATENT AND TRADEMARK OFFICE
CERTIFICATE OF CORRECTION

PATENT NO. : 4,520,014
DATED : May 28, 1985
INVENTOR(S) : Peter Martin Newsome et al.

It is certified that error appears in the above-identified patent and that said Letters Patent are hereby corrected as shown below:

On the title page the "Notice" should read

-- The portion of the term of this patent subsequent to June 1, 1999 has been disclaimed --.

Signed and Sealed this

Seventeenth Day of June 1986

[SEAL]

Attest:

Attesting Officer

DONALD J. QUIGG

Commissioner of Patents and Trademarks